United States Patent
Drnevich et al.

(10) Patent No.: US 7,041,271 B2
(45) Date of Patent: May 9, 2006

(54) INTEGRATED OLEFIN RECOVERY AND HYDROGEN PRODUCTION FROM REFINERY OFF-GASES

(75) Inventors: Raymond Francis Drnevich, Clarence Center, NY (US); Jeffrey O. Herzog, The Woodlands, TX (US)

(73) Assignee: Praxair Technology, Inc., Danbury, CT (US)

( * ) Notice: Subject to any disclaimer, the term of this patent is extended or adjusted under 35 U.S.C. 154(b) by 680 days.

(21) Appl. No.: 10/267,840

(22) Filed: Oct. 10, 2002

(65) Prior Publication Data

US 2004/0073076 A1    Apr. 15, 2004

(51) Int. Cl.
*C01B 3/02* (2006.01)
*C01B 3/22* (2006.01)

(52) U.S. Cl. .................. 423/648.1; 423/650; 423/651; 423/652; 423/655; 585/324; 585/330; 585/654; 585/655; 585/658; 585/809

(58) Field of Classification Search ............ 423/648.1, 423/650, 651, 652, 655; 585/324, 330, 654, 585/655, 658, 809
See application file for complete search history.

(56) References Cited

U.S. PATENT DOCUMENTS

| 4,720,293 | A |   | 1/1988 | Rowles et al. ............... 62/24 |
| 5,502,971 | A |   | 4/1996 | McCarthy et al. .............. 62/20 |
| 5,856,607 | A |   | 1/1999 | Kim ........................... 585/448 |
| 6,069,288 | A | * | 5/2000 | Ou et al. ..................... 585/800 |
| 6,307,117 | B1 | * | 10/2001 | Tsunoda et al. ............ 585/651 |
| 6,524,550 | B1 | * | 2/2003 | Chintawar et al. .......... 423/650 |
| 6,677,497 | B1 | * | 1/2004 | Liu ............................. 585/658 |
| 2002/0141938 | A1 | * | 10/2002 | Ruettinger et al. ......... 423/652 |

OTHER PUBLICATIONS

Burke et al., "Ethylene, CW Report Part 2" (1965) pp. 69-81, Chemical Week Nov. 13, 1965.
Lowenheim et al., "Industrial Chemicals, 4$^{th}$ Edition" (1975) pp. 355-364.
Ma, "Ethylene From Refinery Gas" (1981) Report No. 150, Process Economics Program-SRI International.

(Continued)

*Primary Examiner*—Stuart L. Hendrickson
*Assistant Examiner*—Timothy C. Vanoy
(74) *Attorney, Agent, or Firm*—David M. Rosenblum

(57) ABSTRACT

A method is disclosed a method for recovering olefins and for producing hydrogen from a refinery off-gas stream in which such stream is conventionally pretreated and separated to obtain a light ends stream that contains nitrogen, hydrogen and carbon monoxide and a heavy ends stream that contains the olefins. The light ends stream is subjected to reforming and a water gas shift reactions after addition of a natural gas stream. The addition of the natural gas increases the hydrogen recovery from the light ends and also stabilizes the hydrocarbon content in the stream to be subjected to the reforming and water gas shift reactions. The heavy ends can be further treated to recover olefins such as ethylene and propylene. The rate of natural gas addition is controlled so that the concentration of the nitrogen in a stream exiting the water gas shift reactor is less than about 5 percent by volume so that hydrogen separation from such stream becomes practical.

7 Claims, 1 Drawing Sheet

OTHER PUBLICATIONS

Schurz et al., "A 12 MW Gas Turbine Cogeneration Plant Fired With Refinery Gases" (1982) pp. 63-66 .CME Dec. 1982.

Farmer "330-MW Cogen-Merchant Plant Operating On Refinery Residue Gas" (1988) pp. 16-21 Gas Turbine World Mar.-Apr. 1998.

Kraus et al., "Integrating A Cogeneration Plant Into A Refinery" presented at AICHE meeting (1988).

Netzer "Economically Recover Olefins From FCC Offgases" (1997) pp. 83-91 Hydrocarbon Processing Apr. 1997.

* cited by examiner

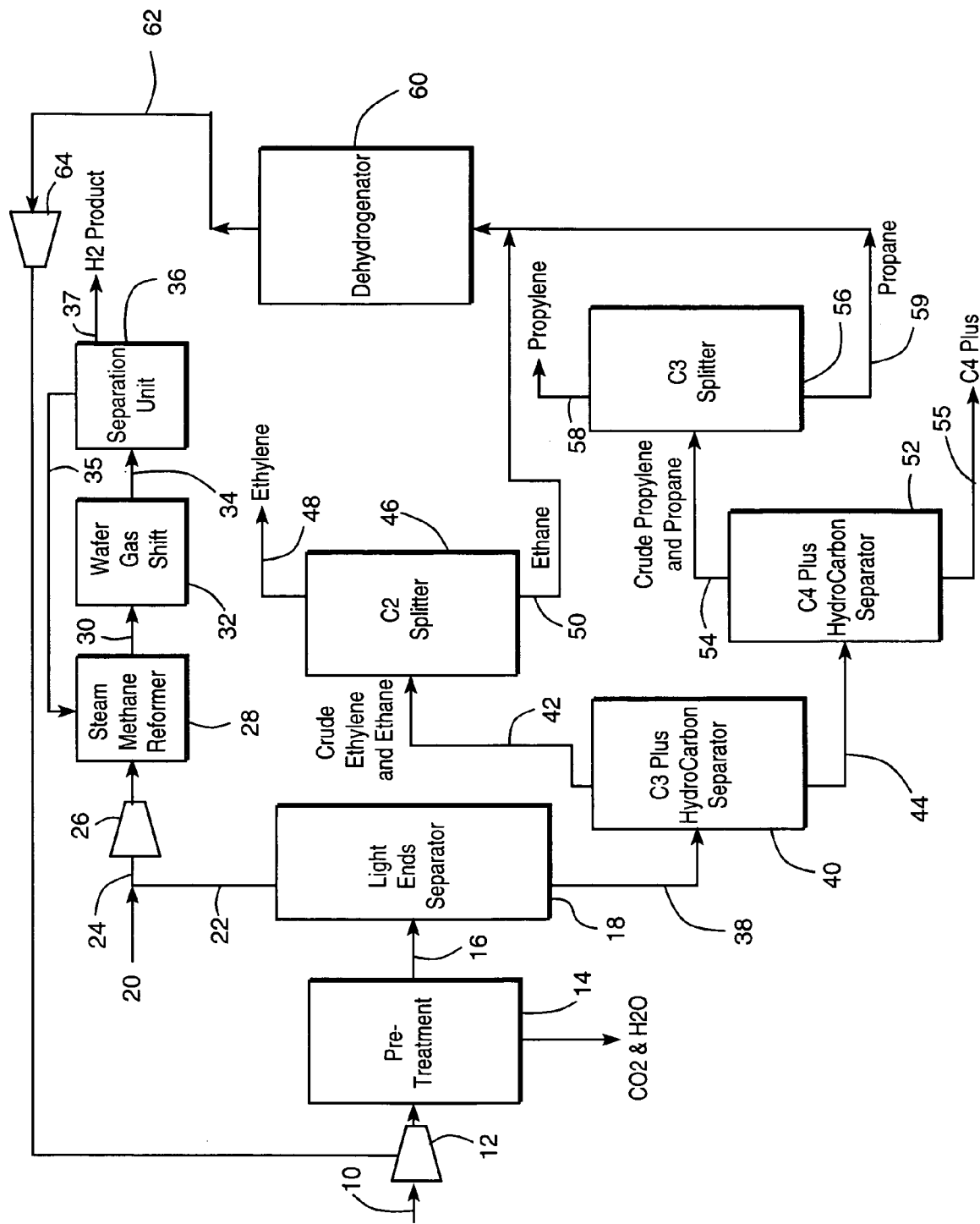

INTEGRATED OLEFIN RECOVERY AND HYDROGEN PRODUCTION FROM REFINERY OFF-GASES

FIELD OF THE INVENTION

The present invention relates to a method of recovering olefins and producing hydrogen from a refinery off-gas in which light and heavy ends contained within the refinery off-gas are separated, the olefins contained within the heavy ends are separated and the light ends are treated to produce additional hydrogen for recovery. More particularly, the present invention relates to such a method in which natural gas is injected into the separated light ends prior to the treatment thereof to produce hydrogen.

BACKGROUND OF THE INVENTION

The petroleum industry has often sought new integration opportunities for its refinery products with other processes. One of the areas of interest concerns refinery gases that are currently used as a fuel. In addition, refineries are processing heavier crude oils and sulfur specifications for both diesel and gasoline products are becoming more stringent. Hydrogen can be used within hydrotreaters to remove sulfur, oxygen, and nitrogen and also within hydrocrackers to produce lighter and more parafinic oils. Consequently, refineries are looking for low cost sources of hydrogen.

While the refinery gases are a potential source of hydrogen, many refinery gas steams are not used either for their hydrogen content or to generate hydrogen through known reforming techniques due to a variety of economic and practical reasons. For instance, the economics for separating hydrogen from refinery gases that contain less than about 30% hydrogen are generally unfavorable. The direct use of refinery gases that contain significant amounts of olefins in steam methane reformer is not practical due to their high sulfur content, low pressure and variable olefin content. Moreover, the use of olefins as a feed to a reformer is problematical in and of itself due to the high probability of carbon formation that occurs with the use of higher order hydrocarbons at high temperatures.

While refinery gases also contain hydrogen, generally the hydrogen concentration within such refinery off-gases is too low for the hydrogen to be economically recovered using current available separation technologies.

The off-gas from a fluidic catalytic cracker unit (an "FCC") is a prime source of olefins and is the focus of prior art efforts for olefin recovery. Generally, the feed stream has a light end content that includes hydrogen, methane, and nitrogen and a heavy end content that comprises ethane, ethylene, propane, propylene, and higher molecular weight hydrocarbons. The off-gas, as a feed stream, is compressed and then pretreated. During pretreatment, a number of operations are performed including, catalytic hydrogenation of acetylene to ethane, catalytic removal of residual molecular oxygen, caustic or amine scrubbing to remove carbon dioxide and hydrogen sulfide, and drying to reduce the water content to acceptable low levels in the parts per million range.

The treated feed stream is then fed to a light end separator to separate the methane, hydrogen and nitrogen from the higher order hydrocarbons including ethane, ethylene, propane and propylene. The light ends separated are used as a fuel gas which is sent to a fuel header. The fuel header is used to distribute fuel to steam generators to generate steam for driving distillation operations such as those used in acid gas removal and for electrical power generation. The olefins contained in the heavy ends are separated in stages, namely ethylene from ethane and propylene from propane.

When the light ends are separated from the heavy ends, the light ends contain hydrogen and nitrogen in nearly equal amounts. Therefore, nitrogen which has no heating value is being added to the fuel header. This is particularly disadvantageous in that the nitrogen absorbs heat from the combustion of the fuel. Furthermore, the piping and other equipment must be sized to accommodate the nitrogen.

There are a variety of known techniques that can be used to separate the nitrogen from the hydrogen. However, the hydrogen content is a relatively small portion of the overall light ends gas stream. This combination of low hydrogen content and high nitrogen content makes the recovery of hydrogen prohibitively expensive because the nitrogen invariably will have to be separated.

The light ends stream also contains methane which is of course a better feed stock than higher order hydrocarbons for reforming operations to generate hydrogen. However, the methane content of the refinery gases is sufficiently variable that it is often not practical to use the light ends stream for such purposes.

As will be discussed, the present invention provides a method of integrating the separation of olefins and the production of hydrogen from a refinery off-gas feed to economically and practically produce the hydrogen while allowing for the separation and disposal of nitrogen.

SUMMARY OF THE INVENTION

The present invention relates to a method of recovering olefins and for producing hydrogen from a refinery off-gas stream. In accordance with the method, the refinery off-gas stream is subjected to a separation process to separate light ends including methane, hydrogen, and nitrogen from heavy end including the olefins, thereby to produce a light ends stream. Natural gas is added in the light ends stream to form a combined stream. The combined stream is subjected to reforming to produce a reformed stream containing carbon monoxide and additional hydrogen. The reformed stream is in turn subjected to a water gas shift reaction to produce an intermediate product stream containing yet additional hydrogen. The hydrogen is separated from the intermediate product stream to produce a hydrogen product stream and a fuel stream containing the nitrogen. The rate of addition of the natural gas stream is controlled so that the amount of nitrogen in the intermediate product stream is less than about 5% by volume on a dry basis.

The addition of natural gas to the light ends stream adds sufficient hydrogen-containing species that the variability of such species in the light end stream does not create difficulties in practically conducting downstream reforming operations because the addition of such stream ensures there will always be sufficient hydrocarbons to conduct the downstream reforming operation. Additionally, after the reforming and water gas shift reactions, the nitrogen concentration is at a sufficiently low percentage that its separation from the hydrogen becomes economically viable in, for instance, a pressure swing adsorption unit. Since, the nitrogen is being separated in a fuel stream, such fuel stream can be burned to generate heat for the reforming of the combined stream. Thus, nitrogen is constantly being removed from the refinery instead of being constantly introduced into the fuel header.

The light ends can be separated from the heavy ends by compressing the refinery off-gas stream and subjecting it to pretreatment. The pretreatment removes carbon dioxide, water and hydrogen sulfide. Thereafter, the separation of the light ends from the heavy ends can be performed by an operation comprising one of low temperature distillation, membrane separation, pressure swing adsorption, and absorption-desorption. The pretreatment comprises catalytic hydrogenation of acetylene to ethane, the catalytic removal of molecular oxygen, caustic or amine scrubbing to remove carbon dioxide and hydrogen sulfide, and drying to remove some of the water content.

After natural gas is added to the light ends stream, the reforming can be steam methane reforming, partial oxidation, or autothermal reforming.

The heavy ends can comprise of ethylene, ethane, propane, propylene and heavier hydrocarbons having a carbon content of four atoms and greater. The ethylene and ethane are separated from the heavy ends to produce a crude ethylene stream comprising ethane and ethylene and a heavier end stream comprising the propylene and propane and yet heavier hydrocarbons. The propylene and the propane can be separated from the heavier end stream to produce a crude propylene stream comprising the propylene and the propane. The ethylene and the ethane of the crude ethylene stream can be separated to produce an ethylene stream and an ethane stream. The propylene and the propane of the crude propylene stream are separated to produce a propylene stream and a propane stream.

The ethane stream and the propane stream can be combined to form a recycle stream. The recycle stream can be subjected to dehydrogenation to convert some of the ethane to ethylene and part of the propane to ethylene and propylene. The dehydrogenation can be accomplished by steam cracking, catalytic dehydrogenation, or oxidative dehydrogenation. The dehydrogenated recycle stream is compressed to allow for its combination with the refinery off-gas stream after the compression thereof.

BRIEF DESCRIPTION OF THE DRAWING

While the specification concludes with claims distinctly pointing at the subject matter that applicants regards as their invention, it is believed that the invention will be better understood when taken in connection with the accompanying sole FIGURE which illustrates a schematic for carrying out a method in accordance with the present invention.

DETAILED DESCRIPTION

With reference to the FIGURE, a feed stream 10 composed of a refinery off-gas is compressed in a compressor 12 to a pressure of about 300 psig. The refinery off-gas can be obtained from a fluidic catalytic cracker, a coker or can be all of the refinery off-gases produced in the refinery. The resultant compressed stream is then pretreated in a conventional pretreatment system 14 that can include a catalytic hydrogenation reactor to convert acetylene to ethane, a unit for the catalytic removal of residual molecular oxygen, for instance a reactor with a sulfided nickel catalyst, a caustic or amine scrubber to remove carbon dioxide and hydrogen sulfide and a drying unit such as a molecular sieve thermal swing adsorption unit to remove the moisture content.

The resultant treated feed stream 16 is then introduced into a light ends separator 18 that serves to separate the light ends from the heavy ends, in other words, methane, hydrogen and nitrogen (light ends) from hydrocarbons having a higher carbon content than the methane (heavy ends) that include the olefins. The separation can be accomplished by a number of known techniques including, low temperature distillation, membrane separation, pressure swing adsorption, and absorption-desorpton.

The foregoing description represents some of the conventional components of a known system to process a refinery off-gas stream for eventual recovery of olefins such as ethylene and propylene. In accordance with the present invention, a natural gas stream 20 is added to the light ends stream 22 to form a combined stream 24. The combined stream 24 is then compressed within a compressor 26 (compressor is optional if light ends are recovered at a high enough pressure for direct addition to the SMR) and is thereafter introduced into a steam methane reformer 28 which could also be, for instance, a partial oxidation reformer or an autothermal reformer. Steam methane reformer 28 converts methane into carbon monoxide and hydrogen.

The product of steam methane reformer 28 as a reformed stream 30 is introduced into a water gas shift conversion unit 32 to form still more hydrogen. An intermediate product stream 34 is recovered from water gas shift conversion unit 32 and introduced into a separator unit 36 to separate the hydrogen from the other components of intermediate product stream 34, namely, nitrogen, CO, $CO_2$, water vapor and residual methane. Such residual products can be extracted from separator unit 36 as a fuel stream 35. Fuel stream 35 can be used in a combustion process, preferably, in steam methane reformer 28 to supply heat to the reforming of combined stream 24. The hydrogen product stream 37 can be introduced into a hydrotreater or hydrocracker.

Preferably, separation unit 36 is a pressure swing adsorption unit. In such a unit, one or more adsorbent beds are pressurized to adsorb the nitrogen and other contaminants and thereby produce a product hydrogen stream. Thereafter the beds are depressurized to desorb the nitrogen and other contaminants and blown down with product to remove any residual nitrogen and other contaminants contained in the beds. Given that light ends stream 22 contains nitrogen and hydrogen in an almost one to one ratio, if hydrogen were attempted to simply be separated from such stream, hydrogen product would be lost to such an extent during bed depressurization and blow down that hydrogen product recoveries would suffer and make the recovery unattractive.

As has been discussed, the addition of the natural gas stream 20 has an overriding advantage of continually supplying sufficient hydrocarbons to make ongoing downstream reforming processes practical. Additionally, the added hydrogen introduced or produced from the natural gas stream 20, the nitrogen content becomes sufficiently low in the intermediate product stream 34 to make the hydrogen separation therefrom economically practical. In this regard, the natural gas stream should be injected at a rate so that the amount of nitrogen in the intermediate product stream is less than about five percent by volume on a dry basis. This degree of control can be exercised by limiting stream 22 to less than about 75% of the feed flow to the reformer.

Table 1 and Table 2, set forth below, are calculated examples illustrating the effects of the addition of the natural gas stream to the light ends stream 22. hydrogen has climbed 2.5 percent and the nitrogen concentration has dropped to 3.1 percent. In this case only about 0.033 moles of nitrogen need to be rejected per mole of hydrogen fed to the separator, more than a 50% improvement compared to Table 1. The impact on PSA recovery would be in the range of about 6% (i.e., 90% versus 84%.)

TABLE 2

Natural Gas Injection (50% of methane from light ends
and 50% of methane from Natural Gas)

| Component | Feed Stream 10 (FCC Off-Gas) Mole % | Natural Gas Mole % | Intermediate Product Steam 54 Mole % |
|---|---|---|---|
| Hydrogen | 15.3 | 0 | 91.9 |
| Nitrogen | 15.3 | .3 | 3.1 |
| Methane | 67.4 | 97.8 | 5.0 |
| Ethane | .5 | 1.3 | 0 |
| Ethylene | 1.4 | 0 | 0 |
| Propane | 0 | 0 | 0 |
| Propylene | 0 | 0 | 0 |
| C4+ | 0 | 0 | 0 |
| Total | 100 | 100 | 100 |

Although not reflected in Table 2, nitrogen impacts the size of the steam methane reforming and the water gas shift reactors.

Olefins, such as ethylene and propylene, are recovered by further processing which has heretofore been used in the prior art for such purposes. For such purposes, a heavy ends stream 38 is introduced into a C3 plus hydrocarbon separator 40 which can be a distillation column system, a membrane system, a pressure swing adsorption system or an adsorption-desorption system. In such a system, a crude ethylene stream 42 is produced that contains ethane and ethylene In Table 1, a calculated example is shown in which the feed stream 10 is processed to produce a light ends stream 22 in which natural gas is not injected. In such case, the hydrogen fed to the PSA is roughly 89.5%. For each mole of hydrogen sent to the recovery unit about 0.066 moles of nitrogen needs to be rejected. This represents more than 50 times the amount of nitrogen that must be removed per unit of hydrogen sent to a PSA when compared to an steam methane reformer operating on a typical natural gas. Since nitrogen is the least readily adsorbed component among the lighter species entering the PSA (other lighter species that are difficult to remove include CO, and methane.) The PSA recovery could be impacted by as much as 15% (i.e. going from 90% to about 75%) by the increased nitrogen content for the same product specification. The reduced recovery results in an increase in capital requirements and a reduction in thermal efficiency.

TABLE 1

No Natural Gas Injection

| Component | Feed Stream 10 (FCC Off-Gas) Mole % | Light Ends Stream 22 Mole % | Intermediate Product Steam 54 Mole % |
|---|---|---|---|
| Hydrogen | 8.0 | 15.3 | 89.5 |
| Nitrogen | 8.0 | 15.3 | 5.9 |
| Methane | 35.2 | 67.4 | 4.6 |
| Ethane | 15.0 | .5 | 0 |
| Ethylene | 13.5 | 1.4 | 0 |
| Propane | 3.3 | 0 | 0 |
| Propylene | 12.0 | 0 | 0 |
| C4+ | 5.0 | 0 | 0 |
| Total | 100 | 100 | 100 |

With reference to Table 2, where natural gas is injected, it can be seen that the percentage of and a heavy ends stream 44 is produced that contains the heavier components, namely propane, propylene and C4 plus hydrocarbons.

The light ends stream 42 is introduced into a C2 splitter 46 to separate the ethylene from the ethane and thereby produce an ethylene-containing stream 48 and an ethane stream 50. The C2 splitter is normally a distillation column. The heavy component stream 44 is introduced into a C4 plus separator 52 to produce a light ends stream 54 containing crude propylene and a heavy ends stream containing hydrocarbons having 4 carbon atoms and greater as a heavy ends stream 55. The light ends, crude propylene stream 54 is introduced into a C3 splitter 56 which can be a distillation column system to produce a propylene stream 58 and a propane stream 59.

In accordance with the present invention, the hydrogen yield and the olefin recovery can be increased yet further by optionally combining ethane stream 50 and propane stream 59 introducing the same into a dehydrogenator 60. Dehydrogenation can be accomplished by steam cracking, catalytic dehydrogenation, or oxidative dehydrogenation. If steam cracking is used, approximately 45 to 50% by weight of the ethane introduced into the cracker will be converted to ethylene. About 40% of the ethane will not be converted. About 30 to 35% by weight of the propane will be converted to ethylene and about 10 to 15% will be converted to propylene. About 10% of the propane will remain in the products from the furnace. The product stream will also contain methane, hydrogen and numerous other components in relatively small quantities.

A product stream 62 obtained from dehydrogenator is cooled and then compressed within a compressor 64 and reintroduced into the compressor for pretreatment. In this manner, more hydrogen is added for the light ends separation while at the same time produces an increase in ethylene production to over two and a half times.

While the present invention has been described with reference a preferred embodiment, as will occur to those skilled in the art, numerous changes, additions and omissions may be made without departing from the spirit and scope of the present invention.

We claim:

1. A method of recovering olefins and for producing hydrogen from a refinery off-gas stream comprising:
    subjecting said refinery off-gas stream to a separation process to separate light ends including methane, hydrogen, and nitrogen from heavy ends including the olefins, thereby to produce a light ends stream;
    adding a natural gas stream to the light ends stream to form a combined stream;
    subjecting the combined stream to reforming to produce a reformed stream containing carbon monoxide and additional hydrogen;
    subjecting said reformed stream to a water gas shift reaction to produce an intermediate product stream containing yet additional hydrogen; and
    separating hydrogen from the intermediate product stream to produce a hydrogen product stream and a fuel stream containing nitrogen;
    the rate of addition of the natural gas stream being controlled so that the amount of nitrogen in the intermediate product stream is less than about five percent by volume on a dry basis.

2. The method of claim 1, wherein said fuel stream is burned to generate heat for the reforming of the combined stream.

3. The method of claim 1 or claim 2, wherein:
subjecting said refinery off-gas stream to pretreatment and performing the separation by an operation comprising one of low temperature distillation, membrane separation, pressure swing adsorption, and absorption-desorption;
said light ends are separated from said heavy ends by compressing said refinery off gas stream;
the pretreatment comprises catalytic hydrogenation of acetylene to ethane, catalytic removal of residual molecular oxygen, caustic or amine scrubbing to remove carbon dioxide and hydrogen sulfide, and drying to remove some of the water content.

4. The method of claim 3, wherein said reforming is steam methane reforming, partial oxidation or autothermal reforming.

5. The method of claim 3, wherein:
said heavy ends comprise ethylene, ethane, propane, propylene and heavier hydrocarbons having a carbon content of four carbon atoms and greater;
said ethylene and ethane are separated from said heavy ends to produce a crude ethylene stream comprising ethane and ethylene and a heavier end stream comprising said propane and propylene and yet heavier hydrocarbons;
said propylene and said propane are separated from said heavier hydrocarbons to produce a crude propylene stream comprising said propylene and said propane
said ethylene and said ethane of said crude ethylene stream are separated to produce an ethylene stream and an ethane stream; and
said propylene and said propane of said crude propylene stream are separated to produce a propylene stream and a propane stream.

6. The method of claim 5, wherein:
said ethane stream and said propane stream are combined to form a recycle stream;
said recycle stream is subjected to dehydrogenation to convert part of the ethane to ethylene and part of the propane to ethylene and propylene;
said recycle stream is compressed and combined with said refinery off-gas stream after the compression thereof.

7. The method of claim 6, wherein said dehydrogenation is accomplished by steam cracking, catalytic dehydrogenation, or oxidative dehydrogenation.

* * * * *